(12) United States Patent
Wu et al.

(10) Patent No.: US 8,361,795 B2
(45) Date of Patent: Jan. 29, 2013

(54) HEPATOPOIETIN AND USE THEREOF

(75) Inventors: Zuze Wu, Beijing (CN); Bingxing Shi, Beijing (CN); Chunping Cui, Beijing (CN); Shaojun Du, Beijing (CN); Danli Wu, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 40 days.

(21) Appl. No.: 12/521,135

(22) PCT Filed: Dec. 21, 2007

(86) PCT No.: PCT/CN2007/003722
§ 371 (c)(1),
(2), (4) Date: Feb. 16, 2010

(87) PCT Pub. No.: WO2008/077311
PCT Pub. Date: Jul. 3, 2008

(65) Prior Publication Data
US 2010/0144628 A1    Jun. 10, 2010

(30) Foreign Application Priority Data

Dec. 26, 2006  (CN) .......................... 2006 1 0156298

(51) Int. Cl.
*C12N 5/06* (2006.01)
*C12N 5/08* (2006.01)
*A61K 38/16* (2006.01)
*A61K 31/70* (2006.01)
*C07K 14/475* (2006.01)

(52) U.S. Cl. ...... 435/375; 435/377; 514/44 R; 514/21.2; 514/7.6; 530/350; 530/399

(58) Field of Classification Search .......................... None
See application file for complete search history.

(56) References Cited

U.S. PATENT DOCUMENTS 5,440,022 A  8/1995 Wu et al.
5,550,037 A  8/1996 Francavilla et al.

FOREIGN PATENT DOCUMENTS

CN  1896100    1/2007
CN  1896100 A  1/2007

OTHER PUBLICATIONS

Cui et al., Hepatology Research, 39:200-206, 2009.*

Blomquist K, et al., "Growth stimulation in the liver and tumour development following intraperitoneal injections of liver homogenates in the rat," Acta Pathol Microbiol Scand, 121(Suppl): 375-382 (1957).
Brennan et al., "Protein ligands to HuR modulate its interaction with target mRNAs in vivo," J Cell Biol, 151(1): 1-14 (2000).
Brody et al., "Identification of sequences required for inhibition of oncogene-mediated transformation by pp. 32," J Biol Chem, 274(29): 20053-20055 (1999).
Chen et al., "Structure of pp. 32, an acidic nuclear protein which inhibits oncogene-induced formation of transformed foci," Mol Biol Cell, 7(12): 2045-2056 (1996).
Hagiya et al., "Cloning and sequence analysis of the rat augmentor of liver regeneration(ALR)gene: expression of biologically active recombinant ALR and demonstration of tissue distribution," PNAS, 91(7): 8142-8146 (1994) with correction published in 1995.
Jun et al., "Progress in research on the family of leucine-rich acidic nuclear protein," Bull Acad Mil Med Sci, 30:369-372 (2006).
LaBrecque et al., "Preparation and partial characterization of hepatic regeneration stimulator substance from rat liver," J Physiol, 248(3): 273-284 (1975).
Li et al., "Molecular identification of IIPP2A, a novel potent heat-stable inhibitor protein of protein phosphatase 2A," Biochemistry, 35(22): 6998-7002 (1996).
Malek et al., "Identification and preliminary characterization of two related proliferation-associated nuclear phosphoproteins," J. Biol. Chem, 265(22): 13400-13409 (1990).
Matsuoka et al., "A nuclear factor containing the leucine-rich repeats expressed in murine cerebellar neuron," Proc Natl Acad Sci USA, 91(21): 9670-9674 (1994).
Opal et al, "Generation and Characterization of LANP/pp. 32 Null Mice," Mole Cell Biol, 24(8): 3140-3149 (2004).
Seo et al., "Regulation of histone acetylation and transcription by INHAT, a human cellular complex containing the set oncoprotein," Cell, 104(1): 119-130 (2001).
Cui et al., "Isolation and functional identification of a novel human hepatic growth factor: hepatopoietin Cn," Hepatology, 47(3):986-995 (2008).
Gatzidou et al., "Insights on augmenter of liver regeneration cloning and function," World Journal of Gastroenterology, 12(31):4951-4958 (2006).
Du et al., "Progress in research on the family of leucine-rich acidic nuclear protein," Bull. Acad. Mil. Med. Sci., 30(4):369-372 (2006) (with translation).

* cited by examiner

*Primary Examiner* — Marianne P Allen
(74) *Attorney, Agent, or Firm* — Fish & Richardson P.C.

(57) ABSTRACT

Provided are a hepatopoietin PCn (HPPCn) and its homologous proteins, which can promote hepatocyte proliferation in vitro, promote liver regeneration in vivo, inhibit the growth of tumor cells and promote the apoptosis of tumor cells. The hepatopoietin PCn (HPPCn) and its homologous proteins are useful for the treatment of acute and chronic liver injury, or the treatment of liver fibrosis.

8 Claims, 2 Drawing Sheets

MEMGRRIHLELRNRTPSDVKELVLDNSRSNEGKLEGLTDESEELEFFSATNVGLTSTA
NLPKLNKLKKLELSDNRVSGGVEALAEKCPNLTHLNLCGNKIKDLSTTEPLKNLENL
KSLDLFNCEVTNLNDYRENVFKL<u>LLPLTYLDGYDRDDK</u>EAPNLDAEGYVEGLDEEEE
DEDEEEYDEDAQVVEDEEEEEGEEEDVSGEEEEDEKGYNDGEVDDEEDEEELREEER
GQKRKGEPEDEGEDDDStop     (SEQ ID NO:1)

Fig. 1

HEPATOPOIETIN AND USE THEREOF

CROSS REFERENCE TO RELATED APPLICATIONS

This application is the U.S. national stage under 35 USC 371 of International Application Number PCT/CN2007/003722, filed on Dec. 21, 2007, the entire contents of which are hereby incorporated by reference.

TECHNICAL FIELD

The present invention relates to the field of biological products and protein drugs, in particular, to an exogenous hepatic regeneration factor, Hepatopoietin PCn (HPPCn). This protein can promote hepatocyte proliferation and liver regeneration, and can inhibit the growth of tumor cells and promote the apoptosis of tumor cells when present in cells, so that it has a potential value of clinical application.

BACKGROUND OF INVENTION

Liver is a viscus having a powerful ability of regeneration in a body. The mechanism of regulation of liver has been searched for more than 100 years. However, the action of the growth factors associated with liver regeneration as known presently, e.g. hepatocyte growth factors (HGF), transforming growth factor-α (TGF-α), and the like, lacks the specificity for liver, and thus it is difficult to explain the organ-specific regulation mechanism of liver regeneration. Therefore, the studies in this field have been focused on the search of novel regulation factors of liver regeneration. In the 1950s, it was discovered that, in mammalian liver, there are some substances capable of regulating its growth[1]. In 1975, LaBrecque et al.[2] for the first time reported that there is a thermostable mixture, which can specifically promote hepatocyte proliferation, in the regenerated liver tissue of rat, and this mixture is referred to as hepatic stimulator substance (HSS). In the mid-1980s, the same kind of factors were discovered in human fetal liver tissue by the inventors, and the corresponding bioactivity, physicochemical properties, purification of proteins and clinical application were systemically studied. Since this kind of factors exhibited an excellent therapeutic effect in the clinical treatment of sever liver injury, and thus they were of great interest and a relevant US patent was obtained in 1995[3]. However, the components therein were not further identified due to the limitation of the techniques for purifying and identifying proteins, which limits the further development and application of such substances. Meanwhile, the molecular cloning of this kind of factors has been studied in many laboratories worldwide. In 1995, Hagiya et al.[4] isolated an augmenter of liver regeneration from the regenerated liver tissue of rat and performed the cloning and expression thereof, and it was discovered that the recombinant augmenter of liver regeneration could promote the liver regeneration of the partially hepatectomized rat, but did not have the activity of stimulating the primary-cultured hepatocytes and the liver cell lines in vitro[5].

In recent years, the inventors isolated a new hepatocyte growth factor from the liver of newborn calf by utilizing several isolation processes, and it has been discovered that this hepatocyte growth factor can promote the DNA synthesis of hepatocyte and has a protective effect against the acute or chronic liver injury. This hepatocyte growth factor is designated as HPPCn. The sequence analysis thereof showed that it belongs to the family of leucine-rich acidic nuclear protein (LANP). LANP is a multifunctional acidic nuclear protein, which is involved in a variety of biological processes including signal transduction, protein degradation, cytoskeletal dynamics, and morphogenesis[6-13]. However, it is not reported that LANP as a growth factor can stimulate hepatocyte proliferation or liver regeneration.

There are more than 120 millions of patients suffering from viral hepatitis, cirrhosis and/or liver cancer in China Therefore, developing an active factor capable of specifically promoting hepatocyte proliferation and liver regeneration, is of significance for the treatment of liver injury due to various causes.

In addition, the malignant tumors, such as liver cancer, and the like, become one of main killers for human health, and thus it is very socially important to inhibit the growth of tumor cells or tumorigenesis.

CONTENT OF THE INVENTION

It has been discovered in the present invention that Hepatopoietin PCn (HPPCn) is a novel hepatocyte growth factor, which is isolated from the liver of newborn calf The corresponding human nucleotide sequence was obtained from a human cDNA library, and expressed in E. coli to obtain a recombinant human HPPCn protein. The essential characters of HPPCn are as follows: (1) it is a member of the leucine-rich acidic nuclear protein (LANP) family, has a molecular weight of about 30 KD, and is sensitive for proteases and thermostable; (2) it can promote the DNA synthesis of the primary-cultured hepatocytes of rat and the liver cell lines in vitro; (3) it can promote the DNA synthesis in the livers of partially hepatectomized mice in vivo; (4) it can protect liver from acute liver injury and liver fibrosis; (5) its overexpression in tumor cells can inhibit the growth of tumor cells.

Therefore, the first aspect of the present invention relates to HPPCn comprising the amino acid sequence set forth in SEQ ID NO: 1. Preferably, the sequence of HPPCn of the present invention is set forth in SEQ ID NO: 1. The present invention also relates to a homolog of HPPCn, which has at least 80%, preferably at least 85%, 90% or 95% of homology with HPPCn of the present invention, and retains the activity of HPPCn of the present invention.

A further aspect of the present invention relates to a nucleic acid molecule encoding HPPCn or homolog thereof.

A further aspect of the present invention relates to a pharmaceutical composition comprising HPPCn protein of the present invention or homolog thereof or a nucleic acid molecule encoding the same. The pharmaceutical composition may optionally further comprise a pharmaceutically acceptable carrier or other conventional auxiliary agent. These carriers and auxiliary agents are within the skill of a person skilled in the art.

A further aspect of the present invention relates to the use of HPPCn protein or homolog thereof or a nucleic acid molecule encoding the same, for the preparation of a medicament used to promote hepatocyte proliferation and liver regeneration, to treat the liver injury due to various causes, to treat liver fibrosis, to inhibit the growth of tumor cells when present in cells, or to treat various tumors.

Preferably, the medicament of the invention is used to treat liver fibrosis or acute or chronic liver injury.

According to the present invention, the term "hepatocyte proliferation" refers to the enhancement of cell division capability of the primary-cultured parenchyma cells derived from liver, normal liver cell lines and hepatoma cell lines, wherein the proliferation capability of cells is measured mainly by detecting the DNA synthesis.

According to the present invention, the term "liver regeneration" refers to the capability of mammalian liver to spontaneously recuperate after injury.

According to the present invention, HPPCn of the present invention can be expressed in *E. coli, Pichia, Saccharomyces cerevisiae* or animal cells.

DESCRIPTION OF THE FIGURES

The following figures are only used to illustrate this invention, but not intended to limit the invention.

FIG. 1 shows the amino acid sequence of HPPCn (SEQ ID NO: 1).

The upper panel shows the induced expression of HPPCn in *E. coli* BL21. 1: negative control; 2: inclusion body protein; 3: soluble protein.

The lower panel shows the purification of HPPCn. 1: inclusion body protein; 2: penetration liquid; 3: product eluted by using eluent; 4: low molecular weight marker.

EXAMPLES

The following examples are used to illustrate this invention, but they are not intended to limit the invention.

Example 1

Production of HPPCn

Figure 2:
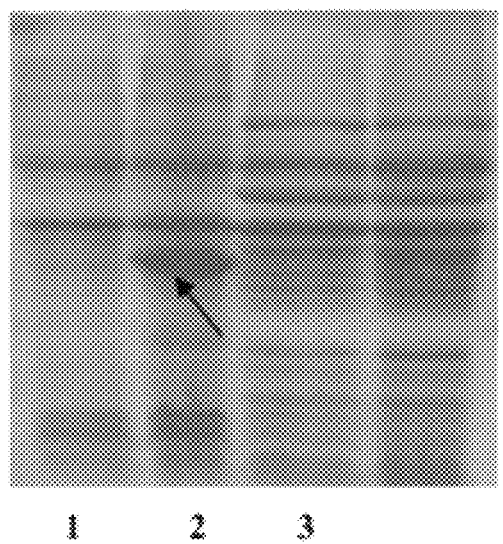
FIG. 2 shows the SDS-PAGE results of the expression of HPPCn in *E. coli* BL21 and of its purification.
Figure 2:
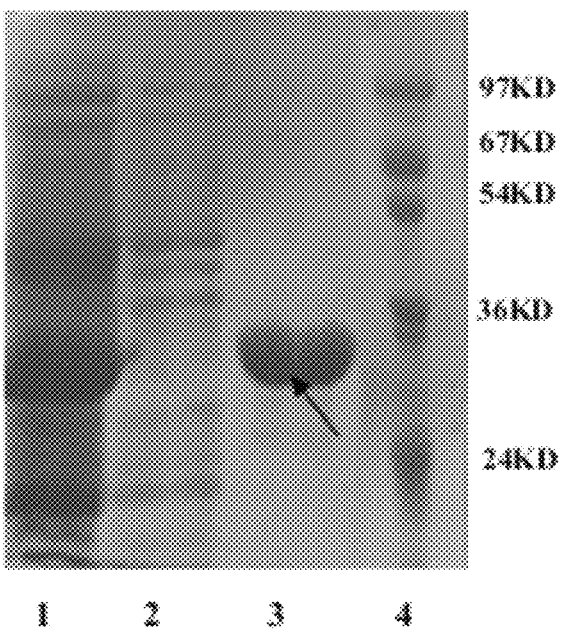

A protein factor, Hepatopoieton PCn (HPPCn), was purified from the liver of newborn calf and was identified, by chromatography such as DEAE cellulose, Source 15Q, and the like; SDS-PAGE recovery; and MALDY-TOF and Q-TOF mass spectrometry. A human HPPCn cDNA sequence was obtained by screening a human fetal liver cDNA library. The BamH I and Xhol I restriction sites were added at both termini of the gene sequence, and then the sequence was constructed into a prokaryotic expression vector PET-24a to obtain the plasmid PET-24a-HPPCn. The plasmid was transformed into *E. coli* and expressed by the IPTG induction. A recombinant protein having a purity of more than 95% was obtained by ion exchange and gel filtration. The amino acid sequence of the protein is shown in FIG. 1, and the electrophoretogram of the protein is shown in FIG. 2.

Example 2

Identification of the Activity of the Recombinant Protein HPPCn to Promote Hepatocyte Proliferation The activity of HPPCn to promote hepatocyte proliferation was detected by $^3$H-TdR DNA incorporation assay. The primary-cultured hepatocytes of rat were used as the target cells in the detection of bioactivity in vitro. 100 µl of cell suspension ($5\times10^4$ cells/ml) were seeded onto 96-well plates and incubated for 6 h. Various concentrations of HPPCn were then added and further incubated for 24 h. $1.85\times10^4$ Bq $^3$H-TdR was added to each well, and 3 h later, a liquid scintillation counting was performed. The results showed that HPPCn can promote the DNA synthesis of hepatocytes in a markedly dose-dependent manner (Table 1). Other augmenters of liver regeneration (ALR) do not possess this character of HPPCn.

TABLE 1

Detection of the activity of the recombinant HPPCn protein to promote the primary-cultured hepatocytes proliferation

| Dose (ng/ml) | Incorporation amount of $^3$H (cpm) |
|---|---|
| 0 | 560 ± 127.10 |
| 10 | 689.33 ± 92.34 |
| 20 | 944.33 ± 271.48 |
| 50 | 1183 ± 241.15 |
| 100 | 1226.33 ± 129.01 |
| 200 | 1190.33 ± 347.74 |

Example 3

Protective Effect of the Recombinant Protein HPPCn against Acute Liver Injury The protective effect of the recombinant protein HPPCn on partially hepatectomized mice was determined by detecting the influence of the recombinant protein HPPCn on the DNA synthesis of liver of the 34% hepatectomized mice. Male C57 mice in well health were subjected to the surgical excision of the middle lobe of liver. 2.5 mg HPPCn/kg body weight or a physiological saline in an equivalent volume was injected into the tail vein of the hepatectomized mice at different time points. After treatment for 18 h, 20 µCi $^3$H-TdR was injected intraperitoneally. After incorporation for 2 h, the animals were sacrificed, and the genomic DNA of liver was extracted. The incorporation amount of $^3$H-TdR was determined with a liquid scintillation counter. The results showed that the incorporation amounts of $^3$H-TdR in the treatment group are higher than those in the physiological saline control group at various time points (Table 2), suggesting that HPPCn can enhance the regeneration ability of the hepatectomized liver.

TABLE 2

Effect of the recombinant HPPCn protein on the DNA synthesis of liver of the 34% hepatectomized mice

| | Incorporation amount of $^3$H (cpm/mg DNA) | |
|---|---|---|
| Time (h) | Recombinant human HPPCn | Physiological saline |
| 24 | 3244 ± 339.4 | 1641.3 ± 944.4 |
| 36 | 4216 ± 1512.7 | 1582.6 ± 179.8 |
| 48 | 6128 ± 736.1 | 4876 ± 867.04 |
| 60 | 4749.66 ± 359.7 | 2775 ± 0 |
| 72 | 3825.333 ± 294. | 2294.66 ± 716.5 |
| 84 | 2962.667 ± 938.2 | 2197.3 ± 823.7 |

After injection with 1 ml $CCl_4$/kg body weight, 30 Balbc mice in well health were randomly divided into 3 groups: Group I, intravenous injection with 1 mg HPPCn/kg body weight; Group II, intravenous injection with 2.5 mg HPPCn/kg body weight; Group III, intravenous injection with 5 mg HPPCn/kg body weight; Group IV, physiological saline control group. The mice were injected once every 12 h. After 48 h, the alteration of aspartate aminotransferase (AST) and alanine aminotransferase (ALT) in blood were detected, and the mice were subjected to a pathological examination. The results showed that the serum levels of AST and ALT in the mice of control group were significantly increased, and a majority of histiocytes of liver necrotized, exhibited the disappearance of cell nucleus and presented vacuolation; while the levels of AST and ALT were recovered to some extent in the mice of HPPCn treatment groups (Table 3), and the number of necrotic hepatocytes and the degree of liver injury were significantly decreased. This suggests that the recombinant protein has a protective effect against the acute liver injury caused by $CCl_4$.

TABLE 3

Effect of the recombinant HPPCn protein on ALT/AST in the serum of mice with acute liver injury induced by $CCl_4$

| Groups | AST (U/L) | ALT (U/L) |
|---|---|---|
| Group IV | 3450.6 ± 239.5 | 3710 ± 177.7 |
| Group I | 2861.6 ± 229.9 | 2915.4 ± 460.7 |
| Group II | 2847 ± 610.4 | 2904.2 ± 636.0 |
| Group III | 2465.8 ± 429.9 | 2177 ± 520.5 |

Example 4

Protective Effect of the Recombinant Protein HPPCn Against Liver Fibrosis

In 40 Wistar rats, a liver fibrosis model was produced by a compound method using ethanol and $CCl_4$. After 4 weeks, the rats were randomly divided into 4 groups: control group, high dose group, medium dose group, and low dose group. The intraperitoneal administration was carried out every day. At week 8, the animals were sacrificed. Blood samples were taken, and the levels of biochemical indicators such as ALT, AST and the like in blood were determined. The liver was removed, and the changes in appearance of liver were observed, the contents of hydroxyproline and malonaldehyde were determined, and histopathological examination was carried out. The results showed that, when compared to the control group, the treatment groups exhibited a decreased level of aspartate aminotransferase (AST) and alanine aminotransferase (ALT) and a significantly reduced content of hydroxyproline (Hyp), while the content of malonaldehyde (MDA) had no marked change (Table 4). The livers of rats in control group presented a gray yellow and had a non-smooth surface with granules, while the livers of rats in treatment groups were relatively ruddy. The results of HE staining and Masson's trichrome staining of liver tissues showed that cell necrosis and lipid deposition occurred, fibrous tissues proliferated, and pseudolobule formed in the livers of rats of the control group; while the proliferation of fibrous tissues was significantly decreased and the hepatocyte necrosis was reduced in the treatment groups, particularly in the medium dose group. This suggests that the administration of the recombinant protein HPPCn can alleviate the liver fibrosis caused by chronic liver injury.

TABLE 4

Protective effect of the recombinant HPPCn protein on rats with liver fibrosis

| Groups | Hydroxyproline | Malonaldehyde | AST (U/L) | ALT (U/L) |
|---|---|---|---|---|
| Normal | 0.15 ± 0.072 | 0.89 ± 1.29 | 17.28 ± 1.49 | 39.71 ± 5.12 |
| Control Group | 1.02 ± 0.418 | 11.45 ± 3.15 | 13.6 ± 3.84 | 85.66 ± 15.90 |
| low dose group | 0.59 ± 0.223 | 10.15 ± 3.75 | 10.28 ± 2.13 | 59.83 ± 6.55 |
| medium dose group | 0.50 ± 0.063 | 11.87 ± 2.23 | 8.57 ± 2.22 | 56.83 ± 8.42 |
| high dose group | 0.49 ± 0.160 | 10.99 ± 2.44 | 9.14 ± 2.47 | 58 ± 7.56 |

Example 5

Inhibition of the Growth of Tumor Cells by HPPCn when Present in Cells

HPPCn was constructed into an eukaryotic expression vector, plasmid pEGFP-N1, which was used to transfect human liver cancer SMMC7721 cell line. After 36 h of culture, the cells were immobilized with 4% paraformaldehyde and 70% ethanol, respectively. After PI staining, the changes of cell cycle were detected by FACS. The results showed that the transfected liver cancer cells had an evident G0/G1 phase arrest, and the proportion of cells in G2/M phase among the transfected liver cancer cells was significantly lower than that of the group transfected with empty plasmid (Group transfected with pEGFP-N1) (Table 5). This suggests that the overexpression of HPPCn in cells can markedly inhibit the growth of hepatoma cells.

TABLE 5

Effect of HPPCn overexpression in SMMC7721 cells on the cell cycle

| Groups | G0-G1 | G2-M | S |
|---|---|---|---|
| Group transfected with pEGFP-N1-HPPCn | 92.59% | 0.12% | 7.28% |
| Group transfected with pEGFP-N1 | 45.67% | 14.42% | 39.91% |

Reference:
1. Blomquist K, et al. Growth stimulation in the liver and tumour development following intraperitoneal injections of liver homogenates in the rat. Acta Pathol Microbiol Scand 1957; 121(Suppl): 375-382.
2. LaBrecque D R, Pesch L A. Preparation and partial characterization of hepatic regeneration stimulator substance from rat liver. J physiol, 1975. 248(3): 273-284.
3. Wu C t, Tu Q, He F C, et al. Hepatokine and methods for its use. United States Patent, 1995. U.S. Pat. No. 5,440,022.
4. Hagiya M, Francavilla A, Polimeno L, et al. Cloning and sequence analysis of the rat augmentor of liver regeneration(ALR)gene: expression of biologically active recombinant ALR and demonstration of tissue distribution. PNAS, 1995, 92(7): 3076-3080.
5. Francavilla A, Hagiya M, Starzl E. Mamalian A L R: human and rat. United States Patent, 1996. 1996 Aug. 27: U.S. Pat. No. 5,550,037.
6. Matsuoka K, Taoka M, Satozawa N, et al. A nuclear factor containing the leucine-rich repeats expressed in murine cerebellar neuron. Proc Natl Acad Sci USA 1994; 91(21): 9670-9674.
7. Malek S N, Katumuluwa A I, and Pasternack G R. Identification and preliminary characterization of two related proliferation-associated nuclear phosphoproteins. J. Biol. Chem 1990; 265(22): 13400-13409.
8. Brody J R, Kadkol S S, Mahmoud M A, et al. Identification of sequences required for inhibition of oncogene-mediated transformation by pp32. J Biol Chem 1999; 274(29): 20053-20055.
9. Chen T H, Brody J R, Romantsev F E, et al. Structure of pp32, an acidic nuclear protein which inhibits oncogene-induced formation of transformed foci. Mol Biol Cell 1996; 7(12): 2045-2056.
10. Li M, Makkinje A, Damuni Z. Molecular identification of I1PP2A, a novel potent heat-stable inhibitor protein of protein phosphatase 2A. Biochemistry 1996; 35(22): 6998-7002.

11. Brennan C M, Gallouzi I E, Steitz J A. Protein ligands to HuR modulate its interaction with target mRNAs in vivo. J Cell Biol 2000; 151(1): 1-14.
12. Seo S B, McNamara P, Heo S, et al. Regulation of histone acetylation and transcription by INHAT, a human cellular complex containing the set oncoprotein. Cell 2001; 104(1): 119-130.
13. Opal P, Garcia J J, McCall A E et al, Generation and Characterization of LANP/pp32 Null Mice, Mole Cell Biol; 24(8): 3140-9.

The invention claimed is:

1. An isolated polypeptide comprising the amino acid sequence SEQ ID NO:1.

2. An isolated nucleic acid, wherein said isolated nucleic acid comprises a nucleic acid sequence encoding the polypeptide of claim 1.

3. A pharmaceutical composition comprising the nucleic acid of claim 2 and a pharmaceutically acceptable carrier.

SEQUENCE LISTING

```
<160> NUMBER OF SEQ ID NOS: 1

<210> SEQ ID NO 1
<211> LENGTH: 245
<212> TYPE: PRT
<213> ORGANISM: Homo sapiens
<220> FEATURE:
<221> NAME/KEY:
<222> LOCATION:
<223> OTHER INFORMATION:

<400> SEQUENCE: 1

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Ser Glu Glu Leu Glu Phe Phe Ser
        35                  40                  45

Ala Thr Asn Val Gly Leu Thr Ser Thr Ala Asn Leu Pro Lys Leu Asn
    50                  55                  60

Lys Leu Lys Lys Leu Glu Leu Ser Asp Asn Arg Val Ser Gly Gly Val
65                  70                  75                  80

Glu Ala Leu Ala Glu Lys Cys Pro Asn Leu Thr His Leu Asn Leu Cys
                85                  90                  95

Gly Asn Lys Ile Lys Asp Leu Ser Thr Thr Glu Pro Leu Lys Asn Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Leu Thr Tyr
    130                 135                 140

Leu Asp Gly Tyr Asp Arg Asp Lys Glu Ala Pro Asn Leu Asp Ala
145                 150                 155                 160

Glu Gly Tyr Val Glu Gly Leu Asp Glu Glu Glu Asp Glu Asp Glu
                165                 170                 175

Glu Glu Tyr Asp Glu Asp Ala Gln Val Val Glu Asp Glu Glu Glu Glu
            180                 185                 190

Glu Gly Glu Glu Glu Asp Val Ser Gly Glu Glu Glu Asp Glu Lys
        195                 200                 205

Gly Tyr Asn Asp Gly Glu Val Asp Asp Glu Asp Glu Glu Leu
    210                 215                 220

Arg Glu Glu Glu Arg Gly Gln Lys Arg Lys Gly Glu Pro Glu Asp Glu
225                 230                 235                 240

Gly Glu Asp Asp Asp
                245
```

4. A method of inhibiting growth of one or more liver tumor cells in culture comprising contacting the cells with an effective amount of the pharmaceutical composition of claim 3.

5. A method of promoting proliferation of a hepatocyte in culture, the method comprising contacting the hepatocyte with an effective amount of the pharmaceutical composition of claim 3.

6. A pharmaceutical composition comprising the polypeptide of claim 1 and a pharmaceutically acceptable carrier.

7. A method of inhibiting growth of one or more liver tumor cells in culture comprising contacting the cells with an effective amount of the pharmaceutical composition of claim 6.

8. A method of promoting proliferation of a hepatocyte in culture, the method comprising contacting the hepatocyte with an effective amount of the pharmaceutical composition of claim 6.

* * * * *